United States Patent [19]
Wu et al.

[11] Patent Number: 5,196,247
[45] Date of Patent: Mar. 23, 1993

[54] COMPOSTABLE POLYMERIC COMPOSITE SHEET AND METHOD OF MAKING OR COMPOSTING SAME

[75] Inventors: Pai-Chuan Wu, Cincinnati, Ohio; Thomas R. Ryle, Burlington, Ky.; Leopoldo V. Cancio, Cincinnati, Ohio

[73] Assignee: Clopay Corporation, Cincinnati, Ohio

[21] Appl. No.: 663,445

[22] Filed: Mar. 1, 1991

[51] Int. Cl.$^5$ .................. B65D 65/128; B32B 5/14; B32B 7/12; B32B 15/04
[52] U.S. Cl. .................. 428/43; 428/171; 428/286; 428/290; 428/350; 428/913; 428/172
[58] Field of Search .......... 428/171, 286, 290, 350, 428/913, 224, 43

[56] References Cited

U.S. PATENT DOCUMENTS

| | | | |
|---|---|---|---|
| 3,454,510 | 7/1969 | Newland et al. | 424/416 |
| 3,484,835 | 12/1969 | Trounstine et al. | 161/130 |
| 3,797,690 | 3/1974 | Taylor et al. | 428/500 |
| 3,901,838 | 8/1975 | Clendinning et al. | 47/37 |
| 3,921,333 | 11/1975 | Clendinning et al. | 47/37 |
| 3,949,145 | 4/1976 | Otey et al. | 428/424.6 |
| 4,016,117 | 4/1977 | Griffin | 526/5 |
| 4,021,388 | 5/1977 | Griffin | 526/5 |
| 4,120,576 | 10/1978 | Babish | 29/117 |
| 4,125,495 | 11/1978 | Griffin | 526/5 |
| 4,218,350 | 8/1980 | Griffin | 264/137 |
| 4,372,311 | 2/1983 | Potts | 428/332 |
| 4,376,147 | 3/1983 | Byrne et al. | 428/220 |
| 4,420,576 | 12/1983 | Griffin | 524/47 |
| 4,503,098 | 3/1985 | Potts | 428/411.1 |
| 4,546,029 | 10/1985 | Cancio et al. | 428/220 |
| 4,686,790 | 8/1987 | Lahalih et al. | 428/518 |

OTHER PUBLICATIONS

*Environmental Sciences and Technology*, pp. 919–925, "Biodegradability of Photodegraded Polymers", Jones et al.

Primary Examiner—George F. Lesmes
Assistant Examiner—Kathryne E. Shelborne
Attorney, Agent, or Firm—Wood, Herron & Evans

[57] ABSTRACT

Compostable polymeric sheets of biodegradable or environmentally degradable polymers are disclosed. These composite sheets may be made by extrusion and are compostable in municipal solid waste treatment facilities.

21 Claims, 1 Drawing Sheet

COMPOSTABLE POLYMERIC COMPOSITE SHEET AND METHOD OF MAKING OR COMPOSTING SAME

BACKGROUND OF THE INVENTION

For several decades it has been a goal of industry to make plastic sheet materials either biodegradable by microorganisms or environmentally degradable by sunlight, moisture, temperature and the like. Usually after environmental degradation, plastic sheet materials are then more susceptible to assimilation by microorganisms. In spite of considerable efforts, our lands are becoming inundated with plastic sheet materials, and articles made therefrom, that will not degrade perhaps for centuries. It is therefore a continuing goal to make plastic sheet materials as fully degradable or compostable as possible. A compostable material is one that undergoes chemical, physical, thermal and/or biological degradation such that it may be incorporated into and is physically indistinguishable from finished compost (humus) and which ultimately mineralizes (biodegrades to $CO_2$, water and biomass) in the environment like other known compostable matter such as paper and yard waste. It would be highly desirable to provide a plastic sheet material that is compostable especially in a municipal solid waste composting facility where it may undergo biodegradation in the presence of heat, moisture and microorganisms.

There is a particular need for compostable plastic sheet material in disposable diapers, under-pads, hygienic pads and the like. These products for practical purposes must satisfy such properties as water impermeability in order to prevent seepage of urine and other human waste products therethrough. In addition, such sheet materials must have sufficient tear, tensile and impact strengths to function in such useful articles. These same properties that make them useful, however, lead to their lack of biodegradability. A few examples of patents directed to biodegradable and environmentally degradable polymer compositions or products include U.S. Pat. Nos. 3,901,838; 3,921,333; 4,016,117; 4,021,388; 4,120,576; 4,125,495; 4,218,350 and 4,420,576.

SUMMARY OF THE INVENTION

This invention is directed to a compostable composite polymeric sheet. The composite sheet comprises (a) a water insoluble and impermeable top film of thermoplastic polymer, (b) a water insoluble bottom layer of thermoplastic polymer and (c) an intermediate film of water soluble polymer for bonding the top film and bottom layer together to form the composite sheet. Each film or layer of thermoplastic polymer is biodegradable or environmentally degradable. The water soluble film facilitates the separation of the top film and bottom layer in the presence of water to enhance degradation. The composite sheets are degradable under the action of heat, water and/or microorganisms.

The composite sheet of this invention is compostable. "Compostable" means that it undergoes chemical, physical, thermal and/or biological degradation such that it may be incorporated into and is physically indistinguishable from finished compost (humus) and which ultimately mineralizes (biodegrades to $CO_2$, water and biomass) in the environment like other known compostable matter such as paper and yard waste. The compostable films and layers of the composite are either biodegradable or environmentally degradable. "Biodegradable" means that the film or layer is susceptible to being assimilated by microorganisms when buried in the ground or otherwise contacted with the organisms under conditions conducive to their growth. "Environmentally degradable" means that the film or layer is capable of being degraded by heat or surrounding environmental elements without microorganisms to a form that ultimately may be biodegradable or mineralizes, i.e., biodegrades to carbon dioxide, water and biomass. With either of these degradable outer films or layers of the composite, an intermediate layer of water soluble polymer bonds them together into a usable sheet for diapers, underpads, packaging films and the like having suitable thickness and strength. The composite of three layers provides adequate thickness and strength for such uses, yet is destructable because of its structure and composition. When subjected to the water of degrading or composting conditions, the water soluble layer of polymer dissolves and disperses whereby the composite sheet breaks apart. The destruction of the composite sheet permits the top film and bottom layers of compostable film to be more readily biodegraded or environmentally degraded.

Composting conditions that enable the chemical, physical, thermal and/or biological degradation of a composite sheet may vary. Where the top and bottom films of compostable polymers are biodegradable, the water soluble intermediate layer permits these films to separate, thereby microorganisms have ready access to all film surfaces for biodegradation. Where the compostable films are environmentally degradable by containing, for example, a heat activatable prodegradant, then the composite is initially subjected to high temperatures on the order of about 45° C. to 90° C., preferably about 60° C. thereby activating the prodegradant to embrittle and degrade the polymeric film thereby permitting reduction to lower molecular weight components or particles that facilitate further reduction to a biomass and ultimately assimilation by microorganisms. The compostable composite sheet is thus especially adapted to be compostable in municipal solid waste composting facilities such that it may be degraded by physical, chemical, thermal and/or biological degradation. It may then be incorporated into and is physically indistinguishable from the finished compost and ultimately mineralizes in the environment like that of known compostable materials in municipal solid waste such as paper and yard waste.

The compostable composite polymeric sheet of this invention, its method of manufacture and compostability will be better understood with reference to the following detailed description.

DETAILED DESCRIPTION OF THE INVENTION

The top film or bottom layer of the composite sheet is made from a suitable thermoplastic polymer that is biodegradable or environmentally degradable as indicated above. A number of biodegradable thermoplastic polymers for forming the water insoluble and impermeable films are known. For example, biodegradable thermoplastic polymers which are suitable in the practice of the invention are of the normally solid oxyalkanoyl polymers or dialkanoyl polymers represented by poly(caprolactone) or poly(ethylene adipate); polysaccharides or modified polysaccharides such as starch-resin compositions that may be film-formed. Suitable thermoplastic polymers of the environmentally degradable type include polyolefin based polymers that may be film-formed into water insoluble and impermeable films for use as barrier materials in the manufacture of many useful articles such as diapers, underpads, packaging, plastic bags and the like. The olefin based polymers include the most common ethylene or propylene based polymers such as polyethylene, polypropylene, and copolymers such as ethylene vinylacetate (EVA), ethylene methyl acrylate (EMA) and ethylene acrylic acid (EAA), or blends of such polyolefins. The olefins thus that may be polymerized alone or in admixture with other ethylenically unsaturated monomers include, e.g., ethylene; propylene; 1-butene; isobutene; 1-pentene; halogenated olefins such as chloroprene; vinyl benzenes and naphthalenes such as styrene or vinyl naphthalene; vinyl or vinylidene halides such as vinyl chloride and vinylidene chloride; vinyl esters such as vinyl acetate and vinyl benzoate; acrylic and methacrylic acids (otherwise known as polyacrylate or methacrylate) and esters or amides thereof; and dienes such as butadiene, isoprene and cyclopentadiene. Other examples of biodegradable or environmentally degradable polymers suitable for use as the top and bottom films or layers in the composite sheet of this invention are known with reference to the above identified patents cited in the background of this invention and these are incorporated herein by reference. At least one of the top or bottom films must be water impermeable in order to serve the function as a barrier film for making the many useful articles. The opposite outer film or layer need not be water impermeable, but must be water insoluble so as to function in the useful environments and protect the intermediate water soluble film. Examples of the water insoluble layers that may be permeable are nonwoven fibrous layers of polyethylene, polypropylene, or other environmentally degradable or biodegradable polymers.

In one form of the composite, a film of environmentally degradable polymer contains a heat activatable prodegradant such as a polyvalent transition metal salt. The salt may be an inorganic or organic salt of a polyvalent transition metal and the organic salts are preferred. Polyvalent transition metals include manganese, iron, cobalt, nickel, zinc, and the salts include iron chloride, zinc chloride, copper nitrate, copper sulfate, manganese stearate, manganese oleate, copper stearate, zinc stearate, iron distearate, and the like. Reference again is made to the patents mentioned in the background of this invention for other prodegradants that may be employed along with accelerators such as poly(styrene-co-butadiene), for example, and other unsaturated polymers and copolymers.

The water soluble intermediate polymer layer of the composite may be formed by any water soluble polymer that will serve to bond the top film and bottom layers together to form sheet materials that have utility in such fields as diapers, pads, packaging and the like. Polymers that dissolve or disperse in water at ambient or elevated temperatures fall into several groups including natural, semi-synthetic and synthetic products. The common property of water solubility makes them especially suitable for formation of the composite film of this invention. Of the natural type of polymers are included various complex carbohydrates, gums and modified polysaccharides. Of the semi-synthetic type are included modified starches (ethers and acetates), chemically treated carboxymethylcellulose, starch-resins and other modified polysaccharides. Of the synthetic type are included polyvinyl alcohol, polyacrylic or methacrylic polymers (otherwise known as polyacrylate or methacrylate polymers), polyacrylamide, polymethoxyethylene, poly(maleic anhydride), ethylene oxide polymers, and the like. The preferred water soluble polymer forming the intermediate layer of the composite sheet is polyvinyl alcohol (PVA). The PVA may be 100% hydrolyzed or partially hydrolyzed, and, thus can be dissolved in water at room temperature or elevated temperature, respectively, depending upon the degree of hydrolysis. Polyvinyl alcohol may be extruded in film form and coextruded with the compostable top and bottom films or nonwoven fibrous layers of polyolefins as described above.

The composite sheet is preferably formed by coextrusion of the top film and intermediate water soluble film; optionally with coextrusion of the bottom layer. The composite may also be made by lamination of the films and layers; or combined coextrusion-lamination techniques. Also, the top or bottom film or layer, as well as the entire composite, preferably has a plurality of post-extruded stretched areas along lines spaced substantially uniformly across the film or composite surface areas and through the depth of the film or composite. The stretched areas are separated by unstretched areas and have a thickness less than the unstretched areas. The stretched areas weaken the film or composite to improve its degradability or compostability while maintaining its water impermeability. The extruded top or bottom film may have a pattern embossed therein and the plurality of stretched areas are post-embossed through the depth of the embossed film.

A method of degrading or composting the composite sheets of this invention involves treating the composite sheet with water to dissolve the intermediate water soluble film. This separates the top film from the bottom layer or film. The resulting components may then be subjected to further biodegradation or environmental degradation at a suitable temperature to degrade said components. This method may also include the further step of heating the composite or the separated top film and bottom layer or film to physically degrade them and render them susceptible to biodegradation. The heating step may be conducted simultaneously with the water solubilization of the intermediate film. This may be accelerated when the film or layer contains a heat activatable prodegradant as described above. Temperatures for degradation will be in a range of about 45° C. to about 90° C., depending of course on whether the films or layers are being biodegraded with microorganisms or are being degraded with higher temperatures to embrittle them for further degradation. Embrittlement may be facilitated by the films, layers or the composites being incrementally stretched to weaken them.

The method of making a compostable polymeric composite sheet of this invention preferably includes coextruding a water insoluble and impermeable top film of thermoplastic polymer and a film of water soluble polymer and combining a water insoluble bottom layer of thermoplastic polymer on the coextrusion side adjacent said water soluble film to form a composite with the top film having the water soluble polymer therebetween. The water insoluble bottom layer may be coextruded with the top film and water soluble film. The bottom layer may also be combined with the coextrusion as a porous web of nonwoven thermoplastic fibers.

The extrusion may be combined with the further step of embossing to form an embossed composite sheet.

As described above, the extrusion method may also be conducted where the film or composite is stretched along lines spaced substantially uniformly across the surfaces thereof and through the depth thereof to weaken the strength of said extruded composite while maintaining its water impermeability.

DETAILED EXAMPLES OF THE INVENTION

The following examples illustrate compostable polymeric composite sheets of this invention and methods of making the composite sheets. In light of these examples and this further detailed description it will become apparent to a person of ordinary skill in the art that variations thereof may be made without departing from the scope of this invention.

The invention will also be further understood with reference to the drawings in which.

Figure 1:
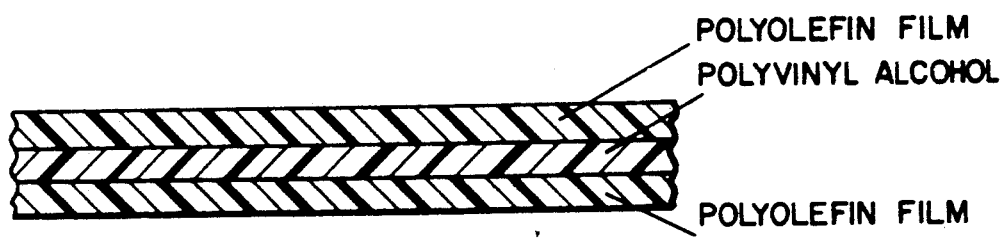
FIG. 1 is a diagrammatic view in cross-section of a compostable polymeric sheet of polyolefin film/polyvinyl alcohol film/polyolefin film.

EXAMPLE I—COMPOSTABLE COMPOSITE SHEETS OF POLYOLEFIN/POLYVINYL ALCOHOL/POLYOLEFIN

A water insoluble and impermeable polymer film for the compostable composite includes the following formulation:

| | |
|---|---|
| Polyethylene, polypropylene, copolymers or blends | 68-98% |
| Manganese stearate | 0.1-7% |
| Poly(butadiene-co-styrene) | 2-20% |
| TiO$_2$ (pigment) | 0-5% |

The above formulation thus contains a polyolefin based polymer with manganese stearate as a heat activatable prodegradant and an unsaturated double polymer of poly(butadiene-co-styrene) as an accelerator. The above thermoplastic film formulation is coextruded with a polyvinyl alcohol. Examples of suitable water soluble polyvinyl alcohol polymer include Vinex 2034, Vinex 1003, Vinex 5030 and Vinex 5020 manufactured by Air Products. Vinex 2034, 5030 and 5020 dissolve in water at room temperature. Vinex 1003 dissolves in water at elevated temperature. For purposes of this example, coextrusion of the water insoluble polyolefin film with the water soluble polyvinyl alcohol film is achieved by the use of a coextrusion feed block located between two separate extruders and a die. The feed block serves to combine the polymer streams flowing from separate extruders into intimate contact with one another to form a single stream and to direct the combined streams in a parallel flow pattern into the die formation of the coextruded composite film. The extruder which delivers the polyvinyl alcohol to the coextrusion feed block and die is normally at a melt temperature of about 340°-400° F., preferably at about 380° F. The extruder which delivers the compostable polyethylene, polypropylene or blend thereof to the coextrusion feed block and die is normally at a melt temperature of about 400°-460° F., preferably at about 430° F. It is to be understood that coextrusion techniques are well known to those versed in the art and need not be discussed in detail. A composite compostable sheet of this example is made by coextruding the compostable polyolefin film on both sides at about 0.25-0.6 mil each in thickness and an intermediate film of polyvinyl alcohol at about 0.25 to about 0.6 mil in thickness.

Typically, depending upon extrusion conditions, a composite film of polyethylene/polyvinyl alcohol/polyethylene at about 0.5 mil each layer can be produced at approximately 100 fpm line speed when a 2½ inch extruder is used for polyvinyl alcohol and 3½ extruder is used for the polyethylene formulation, with screw rpms of 30 and 50, respectively. Polypropylene/polyvinyl alcohol/polypropylene composite sheet is also made according to this procedure.

EXAMPLE II—COMPOSTABLE COMPOSITE SHEETS STRETCHED TO WEAKEN AND FACILITATE COMPOSTABILITY

In a preferred form of the invention, low to medium density polyethylene, for instance, is formed into an embossed compostable composite sheet film by a slot-die extrusion means similar to Example I to form a polyethylene/polyvinyl alcohol/polyethylene composite of about 1.5-2 mils in thickness with each film of about 0.5 mil thickness. For example, the low to medium density polyethylene material and polyvinyl alcohol are heated and then introduced in a web form through the coextrusion slot into an embossing nip of a steel and rubber roll system. The coextruded plastic material, upon being introduced between the nip of the rolls, is film-formed and at the same time textured with the engraved pattern of the steel embossing roll. Under suitable embossing pressure, for instance of about 75-120 pounds per linear inch, a thin composite film having the embossed design may be produced. In achieving a composite film thickness of between about 0.5-2 mils to about 10 mils, along with the necessary emboss depth of about 1 to about 10 mils, conditions are controlled in a manner well within the skill of those knowledgeable in the art of producing embossed films with the understanding of this invention. The factors which are considered may be varied depending upon the plastic material used and the characteristics to be obtained in the resultant composite film. Thus, process conditions that are obviously controlled to produce embossed film include temperature, pressure exerted between the nip of the embossing roll or system, the depth of the engraved design on the steel roll and the hardness of the rubber roll. Embossing details are disclosed in U.S. Pat. Nos. 3,484,835; 4,376,147 and 4,546,029 and such details are incorporated herein by reference.

The composite or embossed film is then stretched in accordance with incremental stretching techniques described in copending application Ser. No. 07/478,935, filed Feb. 12, 1990 in the names of Pai-Chuan Wu, Thomas R. Ryle, Robert M. Mortellite and J. David Toppen, now abandoned, and the details of such stretching are incorporated herein by reference. One of the stretchers disclosed therein is described as follows:

A. Diagonal Intermeshing Stretcher

The diagonal intermeshing stretcher consists of a pair of left hand and right hand helical gear-like elements on parallel shafts. The shafts are disposed between two machine side plates, the lower shaft being located in fixed bearings and the upper shaft being located in bearings in vertically slidable members. The slidable members are adjustable in the vertical direction by wedge shaped elements operable by adjusting screws. Screwing the wedges out or in will move the vertically slidable member respectively down or up to further engage or disengage the gear-like teeth of the upper intermeshing roll with the lower intermeshing roll. Micrometers mounted to the side frames are operable to indicate the depth of engagement of the teeth of the intermeshing roll.

Air cylinders are employed to hold the slidable members in their lower engaged position firmly against the adjusting wedges to oppose the upward force exerted by the material being stretched. These cylinders may also be retracted to disengage the upper and lower intermeshing rolls from each other for purposes of threading material through the intermeshing equipment or in conjunction with a safety circuit which would open all machine nip points when activated.

A drive means is typically utilized to drive the stationary intermeshing roll. If the upper intermeshing roll is to be disengagable for purposes of machine threading or safety, it is preferable to use an antibacklash gearing arrangement between the upper and lower intermeshing rolls to assure that upon reengagement the teeth of one intermeshing roll always fall between the teeth of the other intermeshing roll and potentially damaging physical contact between addendums of intermeshing teeth is avoided. If the intermeshing rolls are to emain in constant engagement, the upper intermeshing roll typically need not be driven. Drive may be accomplished by the driven intermeshing roll through the material being stretched.

The intermeshing rolls closely resemble fine pitch helical gears. In the preferred embodiment, the rolls have 5.935" diameter, 45° helix angle, a 0.100" normal pitch, 30 diametral pitch, 14½° pressure angle, and are basically a long addendum topped gear. This produces a narrow, deep tooth profile which allows up to about 0.090" of intermeshing engagement and about 0.005" clearance on the sides of the tooth for material thickness. The teeth are not designed to transmit rotational torque and do not contact metal-to-metal in normal intermeshing stretching operation.

B. Stretching Technique

Figure 2:
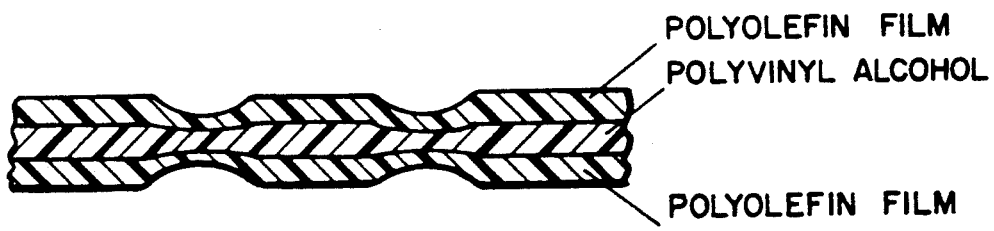
FIG. 2 is a diagrammatic view in cross-section of another form of a composite sheet of FIG. 1 that has a plurality of stretched areas uniformly spaced across and through the depth of the composite for weakening the composite to enhance compostability.

The above described diagonal intermeshing stretcher is employed in this example to produce the incrementally stretched embossed composite plastic sheet that is diagramatically shown in FIG. 2. The stretching operation occurs after the composite sheet is extruded in a manner similar to Example I and has solidified to permit incremental stretching. The woven taffeta pattern in accordance with U.S. Pat. No. 3,484,835 is provided in this example and the composite is incrementally stretched using the diagonal intermeshing stretcher. Upon stretching with one pass through the diagonal intermeshing stretcher with a depth of roller engagement at about 0.085", post-embossed stretched areas are obtained. The original emboss in the unstretched areas is mostly intact. During the stretching process, the thin areas will stretch preferentially to the thick areas due to the lower resistance to the stretching force. In addition, the stretching process weakens and increases the overall area of the composite by about 44%. The area increase effected by diagonal stretching consists of dimensional increases in both the machine and cross direction. The weakened composite sheet enables degradation or composting to occur more readily yet the sheet is impermeable to water so as to function as a water barrier backsheet for diapers and pads.

EXAMPLE III—COMPOSTABLE COMPOSITE OF POLYOLEFIN FILM/POLYVINYL ALCOHOL/NONWOVEN FIBROUS POLYOLEFIN

Figure 3:
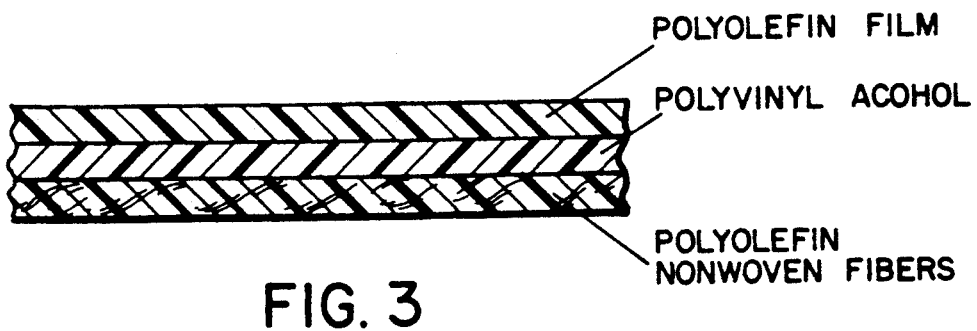
FIG. 3 is a diagrammatic view in cross-section of another form of a composite sheet of polyolefin film/polyvinyl alcohol film/polyolefin nonwoven fibers.

Employing the same coextrusion procedures of Example I with the embossing nip arrangement of Example II, a compostable composite sheet is formed by coextruding a polyethylene or polypropylene film with polyvinyl alcohol (PVA) and, while conducting the coextrusion, a compostable nonwoven fibrous web of polyethylene or polypropylene having the composition of Example I is unwound into the embossing nip at about 40–60 psi to produce a composite structure of about 1 to about 5 mils in thickness. Such a composite is shown diagrammatically in FIG. 3. For example, when a 2½ inch extruder is used for the water soluble PVA and a 3½ inch extruder is used for the compostable polyethylene or polypropylene formulation, the respective screw rpms are about 60 and 20, respectively. As indicated above, a composite film of polyethylene and PVA having about 0.5 mil thickness for each layer can be produced at approximately 100 fpm. The nonwoven fibrous web may be readily unwound into the embossing nip to produce the composite structure. In this composite structure, the nonwoven compostable polyethylene or polypropylene porous fiber web acts as a water insoluble barrier to the underlying water soluble polyvinyl alcohol to protect it during use, for example, in diapers or pads. The composite sheet provides adequate strength, tensile and thickness and yet the polyvinyl alcohol is water soluble thereby aiding in the degradation or compostability of the composite sheet when exposed to the conditions of water, heat and/or microorganisms.

EXAMPLE IV—COMPOSTABLE COMPOSITE OF NONWOVEN FIBROUS POLYOLEFIN/POLYVINYL ALCOHOL/NONWOVEN FIBROUS POLYOLEFIN

The procedure of Example III is repeated except that a single 2½ inch extruder is used at a screw rpm of about 90 rpm with a line speed at about 80 fpm to produce a water soluble polyvinyl alcohol (PVA) film at approximately 1 mil. While extruding the PVA film, two compostable nonwoven fibrous webs of polyethylene or polypropylene of about 2 to 5 mils thickness are unwound into the embossing nip at a pressure of about 40–60 psi to produce a laminated structure of nonwoven fibrous polyethylene or polypropylene/PVA/nonwoven fibrous polyethylene or polypropylene.

EXAMPLE V—COMPOSTABLE COMPOSITE OF POLYCAPROLACTONE/POLYVINYL ALCOHOL/POLYCAPROLACTONE in this Example, polycaprolactone (Union Carbide Tone Polymer P-787) is substituted for the compostable composition of Example I. The polycaprolactone (PCL) is a biodegradable material that does not require the heat activatable prodegradant. Air Products Vinex 2034 polyvinyl alcohol (PVA) was employed as the water soluble material. The melt temperature of the polycaprolactone is about 280°-370° F., preferably at about 300° F. and during the extrusion of the PVA at about 360°-400° F., preferably at about 380° F., the composite sheet is produced. The composite sheet of PCL/PVA/PCL provided a completely biodegradable sheet having water barrier films on both sides of the composite with an intermediate water soluble film. The PVA provides for odor retention and, thus, this composite is especially adaptable for containing or preventing the passage of urine through the composite while reducing the odor in medical applications.

EXAMPLE VI—STARCH-RESIN/POLYVINYL ALCOHOL/STARCH-RESIN

The procedures of Example I are again employed except that a biodegradable starch-resin (Novamont AF05H) is employed for coextrusion with the polyvinyl alcohol (PVA). The melt temperature of the starch-resin is at about 300°-320° F., preferably at 310° F., while PVA is at about 340°-360° F., preferably at about 350° F. The composite sheet produced is a completely biodegradable sheet in the presence of water and microorganisms and can be used in medical applications.

EXAMPLE VII—COMPOSTING COMPOSITE DIAPER BACKSHEETS OF EXAMPLE I

Diaper backsheets are made from composite sheets of Example I formulation. The diaper backsheet is made by coextrusion of polyethylene/polyvinyl alcohol (PVA)/polyethylene composite at about 0.5 mil thickness of each film. Thus, strength and thickness are achieved by the composite for diaper use. The average molecular weight of the polyethylene film is about 77–86,000 and when subjected to a temperature of about 60° C. and 86% RH, the polyethylene films degrade to a lack of mechanical properties, i.e., a plastic dust where the plastic has an average molecular weight of about 1860. When subjected to water of composting conditions the composite breaks apart because of dissolution of the PVA.

It also is known in the literature ("Biodegradability of Photodegraded Polymers", Philip H. Jones et al, *Environmental Science and Technology*, Vol. 8, No. 10, pp. 913-923 (1974)) that once the degree of depolymerization has proceeded to fragments with molecular weight of less than 2000 true biodegradation may occur by Pseudomonas, Alcaligenes, Achromobacter, Flavobacterium and Gamella as gram-negative bacteria, and Arithrobacter, Aerococcus, Cellumonae and an Asporogeneous bacillus, being gram-positive. All of these bacteria are common in soils. Other bacteria in a composting pile may include Azotobactus, Bacillus, Clostridium, Micrococcus, Pseudomonas Fungi, Aspergillus, Peniccillum, Nocardia, Streptomycetes and Thermoactinomyces.

When polypropylene is substituted for polyethylene in the above composite, a film of 136,000 average molecular weight will degrade to a molecular weight of about 2210 at about 60° C. and 86% RH, i.e., a plastic dust. Composting may proceed in the presence of water as indicated above with polyethylene for destruction of the composite.

In the above examples, the compostable polymer film or layer in accordance with this description is one that undergoes chemical, physical, thermal and/or biological degradation in the presence of water, microorganisms and/or heat. Thus, a municipal solid waste composting facility may be used to provide the conditions of heat, microorganisms and water at a temperature sufficient to maintain the viability of the microorganisms, for instance about 45°-70° C., so that they may assimilate organic material and degrade it to a state that is indistinguishable from compost or humus and that ultimately may be mineralized in the environment at a rate equivalent to known compostable materials in municipal solid waste such as paper and yard waste. Ultimately, the compost mineralizes, i.e., biodegrades to carbon dioxide, water and biomass. The polyvinyl alcohol of the composite is biodegradable in the presence of moisture and at ambient or elevated temperatures. Other biodegradable polymers would include modified starches such as starch-resin and polycaprolactone. These polymers are "biodegradable" in that degradability is brought about by living organisms. On the other hand, compostable polyolefin films in accordance with the above examples are degraded by heat. For example, the above polypropylene or polyethylene films or porous fibrous webs containing the heat activatable prodegradant tend to crumble or embrittle, thereby facilitating further degradation and further physical, chemical and/or biological degradation. The temperatures of compostability or degradation will vary from ambient up to about 90° C., or even higher, depending upon whether living organisms were necessary to the degradability of the composite sheet. This invention is not limited to any particular class of microorganisms, rather any suitable miroorganism may be employed.

Having described this invention and its various embodiments and parameters, other variations will become apparent to a person of ordinary skill in this art.

What is claimed is:

1. A compostable polymeric composite sheet comprising
   a water insoluble and impermeable top film of thermoplastic polymer,
   a water insoluble bottom layer of thermoplastic polymer and
   an intermediate film of water soluble polymer for bonding said top film and bottom layer together to form said composite sheet, each of said films or layer being biodegradable or environmentally degradable, said water soluble film facilitating the separation of the composite in the presence of water for exposure of the top film and bottom layer to enhance degradation,
   wherein said sheet is formed by coextrusion of said top film and said intermediate film, said top film has a plurality of post-extruded stretched areas along lines spaced substantially uniformly across the film surface areas and through the depth of the film, said stretched areas being separated by unstretched areas and having a thickness less than the unstretched areas, said stretched areas for weakening said film to further enhance its degradation while maintaining its water impermeability.

2. The composite sheet of claim 1 wherein said bottom layer of thermoplastic polymer is a water impermeable film.

3. The composite sheet of claim 1 wherein said bottom layer comprises a porous web of nonwoven thermoplastic fibers.

4. The composite sheet of claim 1 wherein said extruded top film has a pattern embossed therein and said plurality of stretched areas are post-embossed through the depth of the embossed film.

5. The composite sheet of claim 1 wherein said thermoplastic polymer is a polyolefin based polymer.

6. The composite sheet of claim 5 wherein said polyolefin based polymer is selected from the group consisting of polyethylene, polypropylene, ethylene vinyl acetate, ethylene methyl acrylate, ethylene acrylic acid, and copolymers or blends thereof.

7. The composite sheet of claim 1 wherein said water soluble polymer is selected from the group consisting of polyvinyl alcohol, polymethoxyethylene, polysaccharide, polyacrylamide, polyacrylate, polymethacrylate, poly(maleic anhydride) and modified polysaccharide.

8. The composite sheet of claim 1 wherein both the top film and bottom layer of thermoplastic polymer is selected from the group consisting of polyethylene, polypropylene, polycaprolactone, starch-resin polymer, and co-polymers or blends thereof and the water soluble polymer is polyvinyl alcohol.

9. The composite sheet of claim 8 wherein said top film thermoplastic polymer and polyvinyl alcohol are coextruded.

10. The composite sheet of claim 1 wherein both the top film and bottom layer of thermoplastic polymer is a polyolefin based polymer containing a heat activatable prodegradant.

11. The composite sheet of claim 10 wherein said heat activatable prodegradant comprises a transitional metal salt catalyst.

12. The composite sheet of claim 11 wherein said metal salt is selected from the group consisting of manganese, cobalt and mixtures thereof.

13. The composite sheet of claim 11 wherein said prodegradant also includes an accelerator.

14. The composite sheet of claim 13 wherein said accelerator is an unsaturated polymer.

15. A water impermeable compostable composite polymeric backsheet for diapers and sanitary pads comprising
a water insoluble and impermeable top film of thermoplastic polymer,
a water insoluble bottom layer of thermoplastic polymer and
an intermediate film of water soluble polymer for bonding said top film and bottom layer together to form said composite sheet, each of said films or layer being biodegradable or environmentally degradable, said water soluble film facilitating the separation of the composite of the presence of water for exposure of the top film and bottom layer to enhance degradation, said composite having a thickness of about 0.5 to about 10 mils,
wherein said sheet is formed by coextrusion of said top film and said intermediate film of water soluble polymer, said sheet having a plurality of post-extruded stretched areas along lines spaced substantially uniformly across the sheet surface areas and through the depth thereof, said stretched areas being separated by unstretched areas and having a thickness less than the unstretched areas, said stretched areas for weakening said sheet to enhance its degradation while maintaining its water impermeability.

16. The backsheet of claim 15 wherein said bottom layer of thermoplastic polymer is a water impermeable film.

17. The backsheet of claim 15 wherein said bottom layer comprises a porous web of nonwoven thermoplastic fibers.

18. The backsheet of claim 15 wherein said sheet is laminated during extrusion to a bottom layer of a porous web of nonwoven thermoplastic fibers.

19. The backsheet of claim 15 wherein said bottom layer is coextruded with said top and intermediate films.

20. The backsheet of claim 15 wherein said extruded top film has a pattern embossed therein and said plurality of stretched areas are post-embossed through the depth of the embossed film.

21. The backsheet of claim 15 wherein both the top film and bottom layer of thermoplastic polymer is a polyolefin based polymer and said water soluble polymer is polyvinyl alcohol.

* * * * *